US009285788B2

(12) United States Patent
Nicoletti et al.

(10) Patent No.: US 9,285,788 B2
(45) Date of Patent: Mar. 15, 2016

(54) SMART GARMENT AND METHOD FOR DETECTION OF BODY KINEMATICS AND PHYSICAL STATE

(71) Applicant: RAYTHEON BBN TECHNOLOGIES CORP., Cambridge, MA (US)

(72) Inventors: Michael John Nicoletti, Johnston, RI (US); Scott Evan Ritter, Sudbury, MA (US); Jacob Stuart Michael Beal, Iowa City, IA (US); Matthew Patrick Daily, Portsmouth, RI (US); Jason David Holmes, Easton, MA (US); Christopher Glenn Park, Acton, MA (US)

(73) Assignee: Raytheon BBN Technologies Corp., Cambridge, MA (US)

( * ) Notice: Subject to any disclaimer, the term of this patent is extended or adjusted under 35 U.S.C. 154(b) by 382 days.

(21) Appl. No.: 13/971,678

(22) Filed: Aug. 20, 2013

(65) Prior Publication Data

US 2015/0057984 A1    Feb. 26, 2015

(51) Int. Cl.
| | | |
|---|---|---|
| G06G 7/48 | (2006.01) | |
| G05B 15/02 | (2006.01) | |
| G06T 17/00 | (2006.01) | |
| A61B 5/00 | (2006.01) | |
| A61B 5/11 | (2006.01) | |

(52) U.S. Cl.
CPC ............ *G05B 15/02* (2013.01); *A61B 5/1123* (2013.01); *A61B 5/4585* (2013.01); *A61B 5/4595* (2013.01); *A61B 5/6804* (2013.01); *G06T 17/00* (2013.01)

(58) Field of Classification Search
CPC ............ A41D 13/1281; A61B 5/1127; A61B 5/4595; A61B 5/1123; A61B 5/4855; A61B 5/0804; A61F 5/01; A61N 1/36003; A42B 3/046; B25J 9/1689; G05B 15/02; G06Q 30/0631; G06T 17/00
See application file for complete search history.

(56) References Cited

U.S. PATENT DOCUMENTS

| | | | | |
|---|---|---|---|---|
| 7,602,301 B1* | 10/2009 | Stirling | ............... | A61B 5/1127 340/573.1 |
| 2011/0166491 A1* | 7/2011 | Sankai | ............... | A41D 13/1281 601/84 |
| 2013/0118255 A1* | 5/2013 | Callsen | ................ | A42B 3/046 73/491 |
| 2013/0123568 A1* | 5/2013 | Hamilton | ........... | A61N 1/36003 600/13 |
| 2013/0211594 A1* | 8/2013 | Stephens, Jr. | .......... | B25J 9/1689 700/259 |
| 2014/0052567 A1* | 2/2014 | Bhardwaj | .......... | G06Q 30/0631 705/26.7 |
| 2015/0088043 A1* | 3/2015 | Goldfield | ................. | A61F 5/01 602/6 |

OTHER PUBLICATIONS

Beal, Jacob et al.; "A Spatial Computing Approach to Distributed Algorithms"; 44th Asilomar Conference on Signals, Systems, and Computers; Nov. 2010; 5pp.

* cited by examiner

*Primary Examiner* — Kandasamy Thangavelu
(74) *Attorney, Agent, or Firm* — Lewis Roca Rothgerber Christie LLP

(57) ABSTRACT

A body garment including sensors distributed throughout the garment, each sensor senses body state information from a local surface area of a body; and sensor nodes in proximity to the plurality of sensors, each sensor node including a processor to receive sensing body state information from at least one of the plurality of sensors. Each processor is configured to receive body state information locally from sensors, to utilize the information to determine a local surface shape of the surface of a portion of the body part; and to exchange local surface shape information with neighboring sensor nodes. At least one processor of utilizes the local surface shape information received from the sensor nodes to generate one overall model of a surface shape of the entire surface of the body part covered by the garment.

20 Claims, 7 Drawing Sheets

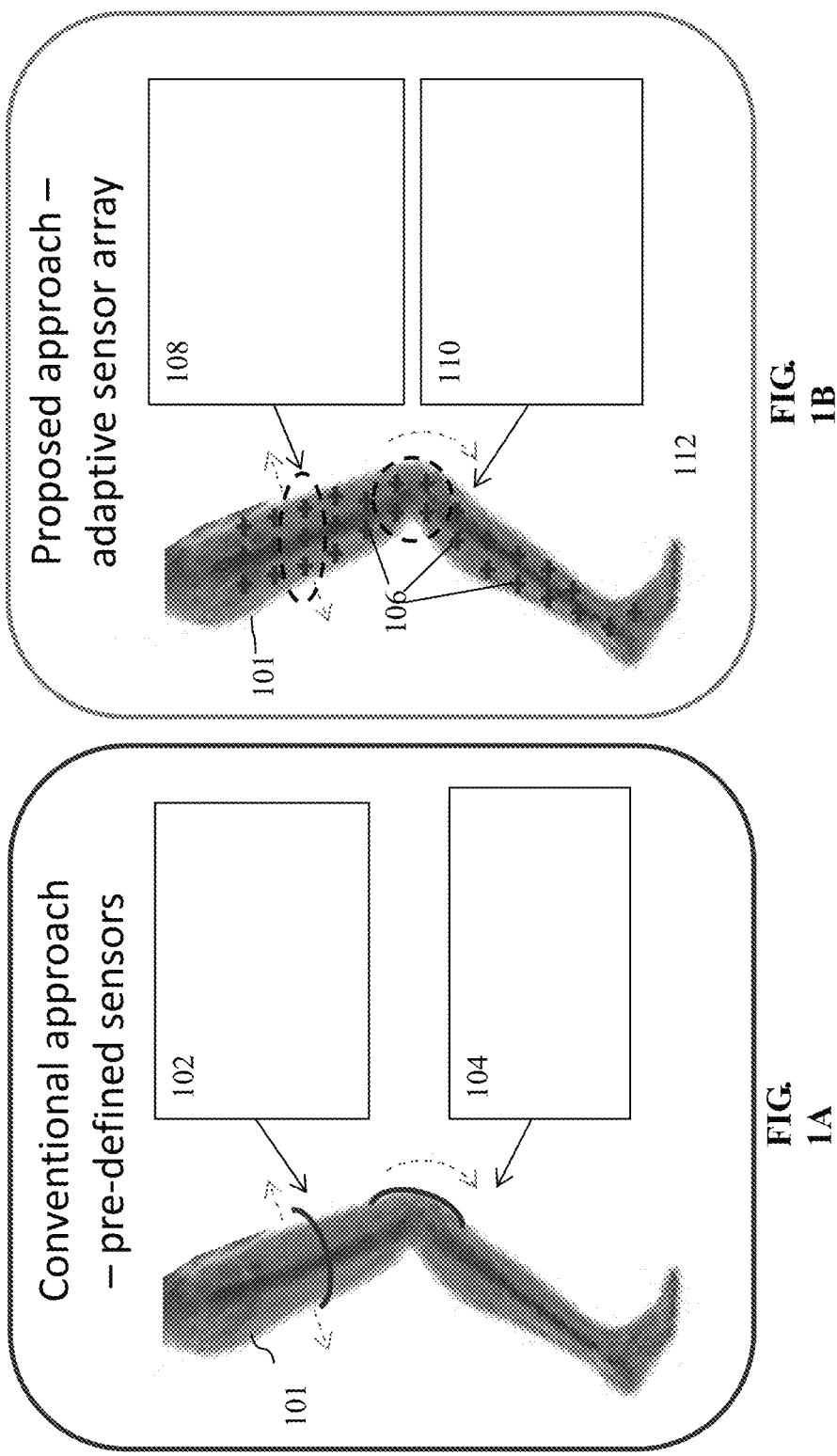

SMART GARMENT AND METHOD FOR DETECTION OF BODY KINEMATICS AND PHYSICAL STATE

FIELD OF THE INVENTION

The present invention relates to sensors and electronic circuits, and more specifically to a smart garment/suit for detection of body kinematics and physical state and a method thereof.

BACKGROUND

Conventional full body bio-mechanical measurement systems use cameras and/or rigidly affixed sensors, for example on or around a treadmill to get a full body pose picture. However, affixed sensors require restrictive equipment to be used and failures occur when sensors move out of position. Precisely affixed sensors result in poor performance if not placed precisely or if their position changes while in use. Similarly, static camera positions pose the problem of not allowing for many behaviors/movements to take place while measurement is occurring, due to a limited field of view or restrictions imposed by treadmill size and speed and static direction. None of these methods/systems are compatible with field maneuvers and during complex athletic maneuvers by a subject while performing in the target environment, for example, during a mission of a soldier.

SUMMARY OF THE INVENTION

In some embodiments, the present invention is directed to a smart garment and a method thereof for detection of body kinematics and physical states, which incorporates many sensors affixed to the suit. The invention optimally uses data from these sensors to derive body state information, such as pose, motion and muscle activation. The invention is capable of collecting and processing data in real time for control of a variety of applications that require pose, activation or movement as inputs. Examples of such applications include actuator interfaces for mechanical assisting, haptic feedback devices for delivering injury warnings, biomechanical systems designed to analyze metabolic activity or athletic load endured by the subject, prosthetic limbs and assistance devices, and health monitoring systems.

In some embodiments, the present invention is a body garment for detecting body kinematics. The body garment includes a plurality of sensors distributed throughout the garment, each sensor being configured to sense body state information from a local surface area of a body part covered by the garment; and a plurality of sensor nodes in proximity to the plurality of sensors respectively, each sensor node including a processor and configured to receive sensing body state information from at least one of the plurality of sensors; wherein each processor is configured to receive body state information locally from one or more sensors in proximity to said each processor; to utilize the information to determine a local surface shape of the surface of a portion of the body part covered by said one or more sensors; and to exchange local surface shape information with neighboring sensor nodes, and wherein at least one processor of at least one sensor node utilizes the local surface shape information received from the sensor nodes to generate one overall model of a surface shape of the entire surface of the body part covered by the garment.

In some embodiments, the present invention is a method for detecting body kinematics. The method includes: collecting body state information from a plurality of local surface areas of a body part covered by a garment, from a plurality of sensors distributed throughout the garment covering the body part; locally and in real time processing the collected body state information of local surface areas to determine a local surface shape of the surface of a portion of the body part covered by respective local surface areas, by a respective one of a plurality of distributed processors; exchanging local surface shape information with neighboring processors; and generating one overall model of a surface shape of the entire surface of the body part covered by the garment from the distributed local surface shape information.

In some embodiments, body kinematics information are generated from the overall model. Furthermore, feedback may be received from the distributed processors or from external devices, and the feedback and the body kinematics information are used to adaptively control an actuator.

BRIEF DESCRIPTION OF THE DRAWINGS

A more complete appreciation of the present invention, and many of the attendant features and aspects thereof, will become more readily apparent as the invention becomes better understood by reference to the following detailed description when considered in conjunction with the accompanying drawings in which like reference symbols indicate like components, wherein:

FIG. 1A shows a conventional hardware configuration for detection of body pose and muscle activation.

FIG. 1B shows an exemplary garment with hardware configuration for detection of body pose and muscle activation, according to some embodiments of the present invention.

DETAILED DESCRIPTION

Figure 1C:
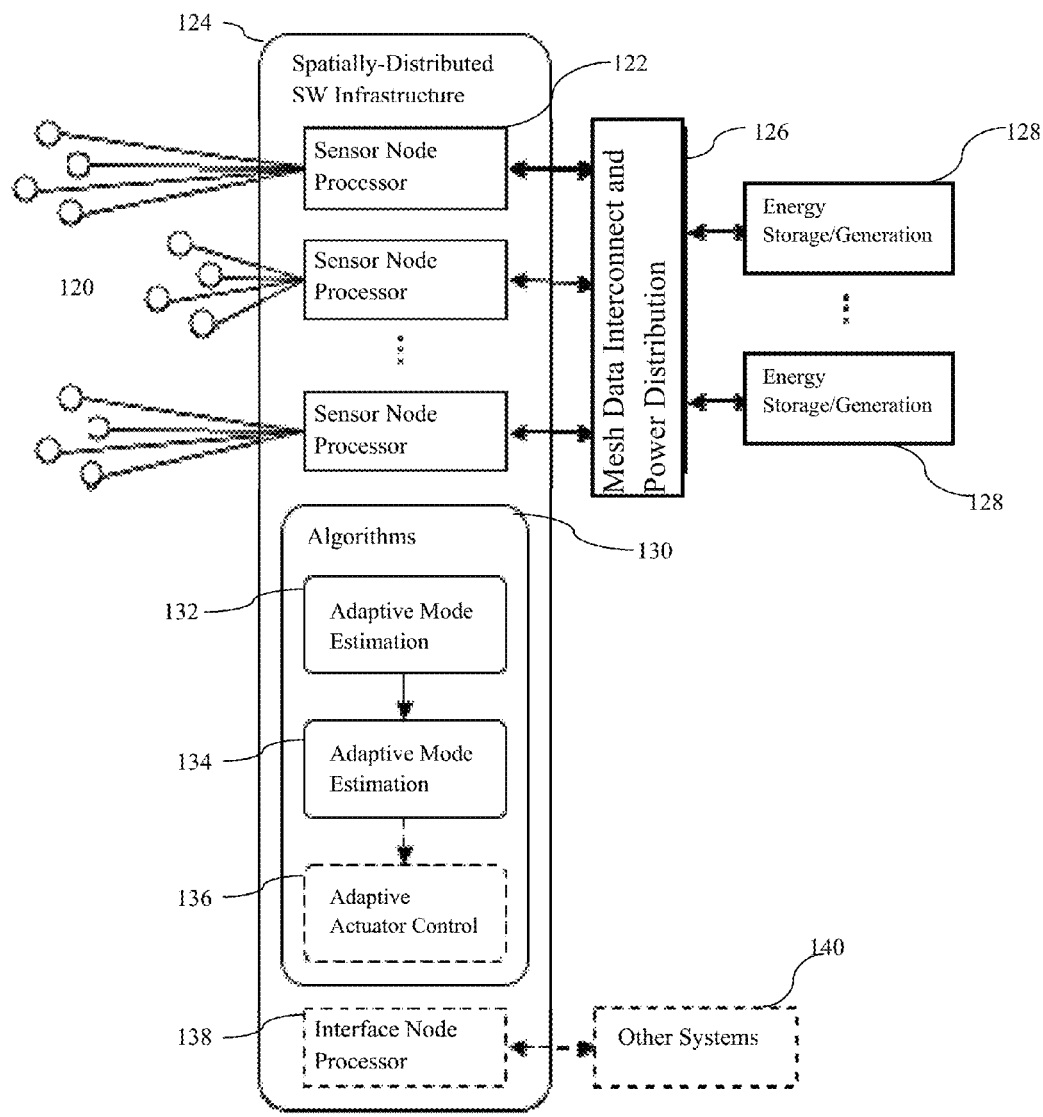
FIG. 1C depicts a simplified exemplary architectural block diagram of a system, according to some embodiments of the present invention.

The present invention is directed to a smart garment/suit for detection of body kinematics and physical state, such as body pose and muscle activation. The invention enables sensor data to be taken anywhere, at any time during any activity of interest. In some embodiments, the present invention comprises of a suit with sensors distributed throughout and especially in places that observe body state information, such as displacement during body movement or activity (for example, athletic movement). State information refers to multiple parameters and features of interest. For example, skin surface temperature, electrical nerve impulses, and whether a person has been at rest or is warmed up. Furthermore, this information can be processed over time to estimate more complex bio-state information such as fatigue and injury.

By using continuous manifold assumptions, data fusion and adaptive algorithm techniques, the invention is capable of losing some fraction of sensors as well as displacement of the sensors on the body and yet perform its desired functions. In this sense, a manifold refers to a set of similar and related sensors that respond in a well ordered distribution. For example, multiple strain sensors over a muscle all deform in a particular pattern when that muscle is contracted. Also, the notion of being adaptive is not limited to simply tailoring to an individual/subject, but to also evolve over time. A continuous algorithm/process is an algorithm/process that operates on data that represents continuous quantities, even though this data is represented by discrete approximations.

In some embodiments, the processing of the sensor data takes place on a centralized processor or a set of distributed processors placed throughout the garment and working in unison to compute the relevant features of the sensor data and advance the kinematic model tracking the body movement. In the case of distributed processing in the garment, the invention is capable of losing some fraction of (distributed) processors and communication links and yet will continue to provide results equal to or of minor degraded fidelity than if the entire suit was intact.

FIG. 1A shows a conventional hardware configuration for detection of body pose and muscle activation. As shown, strain gauges 102 and 104 are placed at specific locations of a leg 101 to measure muscle activation and joint flexure. For example, a circumferential strain gauge 102 is placed around the leg to measure expansion of quadriceps muscle. Similarly, a longitudinal strain gauge (or any sensor capable of measuring the angle of the knee) 104 is placed over the knee cap to measure the knee angle. This data can then be fed to a computer implemented process/algorithm to determine the corresponding quadriceps activation and knee flexure. As described above, these (precisely) affixed strain gauges 102 and 104 result in poor performance if not placed precisely or if their position changes while in use. The resulting data are also descriptive only of the particular muscle and joint angle that are instrumented.

FIG. 1B shows an exemplary garment with hardware configuration for detection of body pose and muscle activation, according to some embodiments of the present invention. As depicted, a plurality of sensors 106 forming one or more meshes are placed throughout the leg 101 to detect body (in this case, leg 101) pose and muscle activation. For example, strain gauge nodes 108 in the upper area of the knee sense and generate related data for elongation in circumferential direction with muscle expansions. Likewise, strain gauge nodes 110 around the knee sense and generate related data for elongation in front and compression in the back of the knee, during knee flex. Pressure sensors at the foot area, for example, at the side and bottom of the foot, sense the pressure exerted on the foot and generate related data.

In some embodiments, muscle activation voltage potentials are sensed by voltage sensors at the skin. Similarly, changes in muscle transmittance may be sensed using optical emitter and receiver (sensor) pair. In some embodiments, circumferential changes in muscle groups are sensed using compliant piezoelectric bands (strain sensors). The plurality of sensors, in combination with the computer implemented process described below, yield data that provide a detailed description of the kinematic joint flexure in multiple axes and the character of actuation (e.g., flexing/extending/twisting) of the muscles that effect the joint.

This data may then be used to distinguish high-dimensional goal manifolds or modes, e.g., the gait of the subject. For example: walking, jogging, running or throwing modes. The data may also be used to analyze the subject's mechanical repeatability or efficiency of a goal, asymmetrical behavior in completion of a goal or metabolic load; using unique processing techniques specific to each feature. The data from the plurality of sensors 106 may also be utilized to detect fitness, injury/malfunction, fatigue, changes due to different weight bearing loads and health of both the subject and the garment. This data can also be used to control a variety of mechanical or robotics actuators, such as a mechanical assist for walking/running or the seamless integration of a prosthetic limb.

FIG. 1C depicts a simplified exemplary architectural block diagram of a system, according to some embodiments of the present invention. As shown data from the sensors 120 are received and locally processed by their respective processors 122 in respective sensor nodes, which are physically interconnected in mesh topology and receive power via the busses and/or channels 126. In some embodiments, the entire system is powered by one or more energy storage/generation components (i.e., batteries, solar cells, thermoelectric generators, etc.) 128. The software running on the processors 122 implements a spatially-distributed infrastructure 124, which may be the Proto™ spatial computing language, that supports data flow and shared processing activity among the discrete processors. It is within this framework that the adaptive, data fusion, and other algorithms 130 are executed. Depending on the particular implementation, these algorithms may include adaptive mode estimation 132, some outputs of which may then support adaptive mode estimation 134. In cases where the invention is used in conjunction with actuators, the outputs of adaptive mode estimation may in turn support adaptive actuator control 136. In some embodiments, an interface node processor 138 is implemented, possibly as an extension to the functionality of a sensor node processor, to communicate with other (external) systems 140.

In some embodiments, the interface to the actuators and their ideal function for use during a mode can be defined in software and uploaded to the system so the on board controller can activate and control the actuator in the most effective way possible. The adaptive nature of the software design also allows for real-time optimization of control algorithms using feedback taken by the suit. In some embodiments, the sensing portion, for example, the garment, may be decoupled from the actuation portion to allow for different actuator applications.

The use of many sensors distributed throughout the garment allows for a robust, compliant solution for a problem conventionally solved by inflexible, rigidly-affixed sensors.

In some embodiments, some of the sensors may be Danfoss PolyPower™ stretch sensors, which are textile compatible capacitive mode sensors. In some embodiments, some of the pressure sensors may be commercial off-the-shelf (COTS) Tekscan™ pressure sensors with resistive load cell technology.

Figure 2:
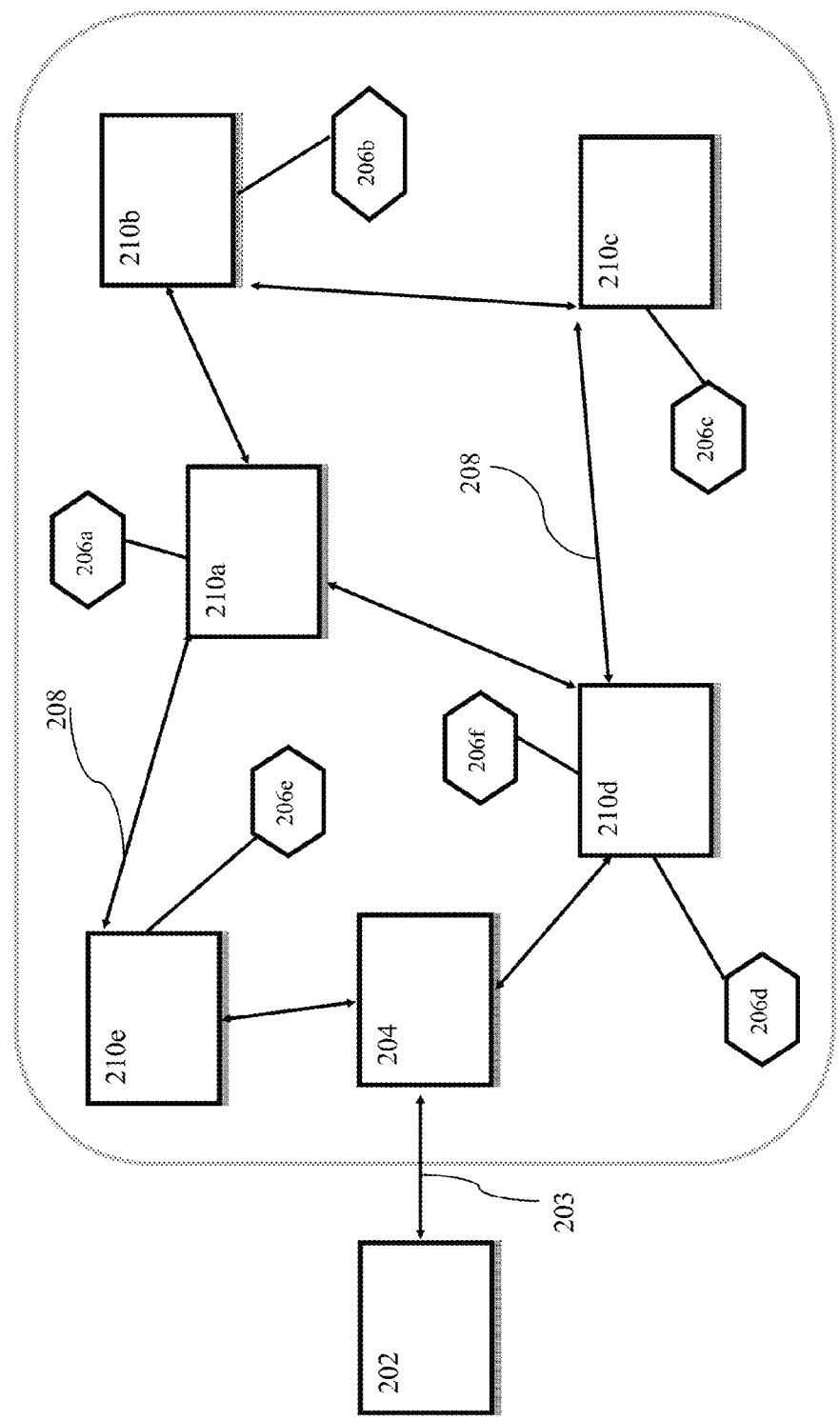
FIG. 2 illustrates a simplified exemplary hardware block diagram of a portion of the garment, according to some embodiments of the present invention.

FIG. 2 illustrates a simplified exemplary hardware block diagram of a portion of the garment, according to some embodiments of the present invention. As shown, a plurality of sensors 206a-206f are placed and distributed throughout the garment and especially in places that observe deformation during body movement or activity. Each sensor 206a-206f is interrogated by a respective sensor node 210a-210e. However, each sensor node 210a-210e may correspond to more than one sensor. The sensors 206 sense muscle expansions and joint activity via modalities that may include but are not limited to myoelectrical, electrical nerve sensors, accelerometers, thermal sensors, optical transmissivity/reflectance, pressure, and/or mechanical strain, and generate related data for its respective sensor node 210. For example, muscular injuries can be detected by increased heat in the region of the injury, sensing nerve impulses and acceleration can result in the kinematic information, and thermal sensors can also provide a sense of fatigue or fatigue potential.

Each sensor node 210 comprises of at least one processor and related hardware and interfaces for processing the sensed signal from its respective sensor(s) and outputting the processed signal to an interface node 204 via way communication channels 208. For example, when the wearer puts on the suit/garment, a series of known callisthenic exercises may take place to calibrate the suit/garment and build a model of body movement, based on the known callisthenic exercises. Once this is done, changes in the manifold is processed to fit the sensor input to the best fit of the body movement model. The holistic body state are then advanced using input from adaptive filters.

In some embodiments, each sensor node is configured to receive body state information locally from one or more sensors in proximity to the sensor node; to utilize the information to determine a local surface shape of the surface of a portion of the body part covered by said one or more sensors; and to exchange local surface shape information with neighboring sensor nodes.

The interface node then sends the processed signal to an external system via a communication channel 203. The processed signal includes kinematics and physical state of the subject's body, such as pose and muscle activation information at each sensor location. Knowing the location of each sensor and its correspondence to body (parts) position and/or muscle provides accurate pose and muscle activation information for the portion of the body covered by the garment. For example, if a sensor is located on the front of the knee to measure strain oriented in a head to toe direction, the increase in strain would correspond to the bending of the knee. Initial calibration provides a range of motion analysis to indicate the maximum strain to be experienced in normal movement, and that initial model is evolved by the adaptive processes running on the system. As another example, if a muscle density sensor or horizontally oriented strain sensor is located on or around the hamstring, the increase in density or strain indicates the muscle is activated.

In some embodiments, the sensor data are used to determine deformation of the epidural manifold over which the suit is worn, that is, the amount of material stretching between points on the garment below and above the knee going from standing to crouching, allowing for the derivation of the joint positions and the state of the muscles and muscle groups of the body. In some embodiments, at least one processor of at least one sensor node utilizes the local surface shape information received from the sensor nodes to generate one overall model of a surface shape of the entire surface of the body part covered by the garment. One skilled in the art would recognize that not all of the peripheral components shown in FIG. 2 are necessary to implement a sensor node, according to the present invention. For example, the functions of the memories; the IO functions; and/or voltage regulation/management functions may be combined together or some of them omitted.

The use of many sensors allows for over-determination of the body position and allows for sensor noise and ambiguity to be mitigated This leads to a high fidelity model of instantaneous body position and muscle activation measurements that can be saved or ex-filtrated to off-board components. The distributed sensors and sensor nodes provide higher fidelity gait information than a typical co-located actuator/sensor can provide, and enable actuator removal/replacement without having to re-design or re-manufacture the garment.

The over-determination also permits the garment to self-configure and to adapt its configuration as the garment shifts on the wearer over time, obviating the need for precise sensor placement. The garment/suit may cover the full-body or partial-body, and the configurations may be implemented as a single garment or multiple dynamically integrated garments, for example, a partial-body garment with multiple components may have disconnected components (e.g., arms and legs but no torso).

In some embodiments, the multiple components of a full body or a partial-body garment may be detachable and attachable to the each other and thus when attached, forming a larger coverage of the body. In these cases, the processors (interface node) of a component are electrically (or optically) coupled with and recognized by the processors (interface node) of the other components, when the component is attached to the other components to cover a larger portion of the body.

In some embodiments, the plurality of sensors 206 and the sensor nodes 210 are configured to be energy efficient. For example, certain sensors (and their respective sensor nodes) located on certain locations of the body/garment, e.g., on certain muscle locations, may be sensing high levels of activity and/or processing in high resolution or high fidelity, while other sensors (and their sensor nodes) positioned on different location of the body/garment may be sensing low levels of activity and/or low resolution/fidelity, thus conserving energy. In other words, the distributed sensor nodes may be running fast and dense in critical areas and slower in stable regions. For example, when an adaptive filter converges on the goal manifold identified as running, any sensors present on the trunk and/or arms would be operating at reduced data (and energy) rates relative to those on the ankles, knees, and/or soles.

In some embodiments, the computations (in the sensor nodes, and/or a central processing location) are specified in terms of geometric computations and information flow. One advantage of this mode of specification is that it can enable automated programming methods, such as those using the amorphous medium continuous abstraction, to automatically generate a robust distributed algorithm implementation of such a specification. For instance, a bend angle may be computed by integration of curvature over the knee region, or fatigue may be measured by gathering the mean frequency of trembling across the region of a leg muscle, or the pose of the body may be computed by flowing the pose information computed in a region (e.g., the knee), to other nearby regions (e.g., upper leg, lower leg, ankle, hip) where it can be fused with the geometry of those regions to create a more abstract model of leg pose. For example, the knee region model may overlap on its edges with the upper leg and lower leg models, which in turn overlap on their other edges with the ankle and hip models. These overlap regions can be used to align the models, allowing construction of a lower-resolution model of the full leg.

Figure 3:
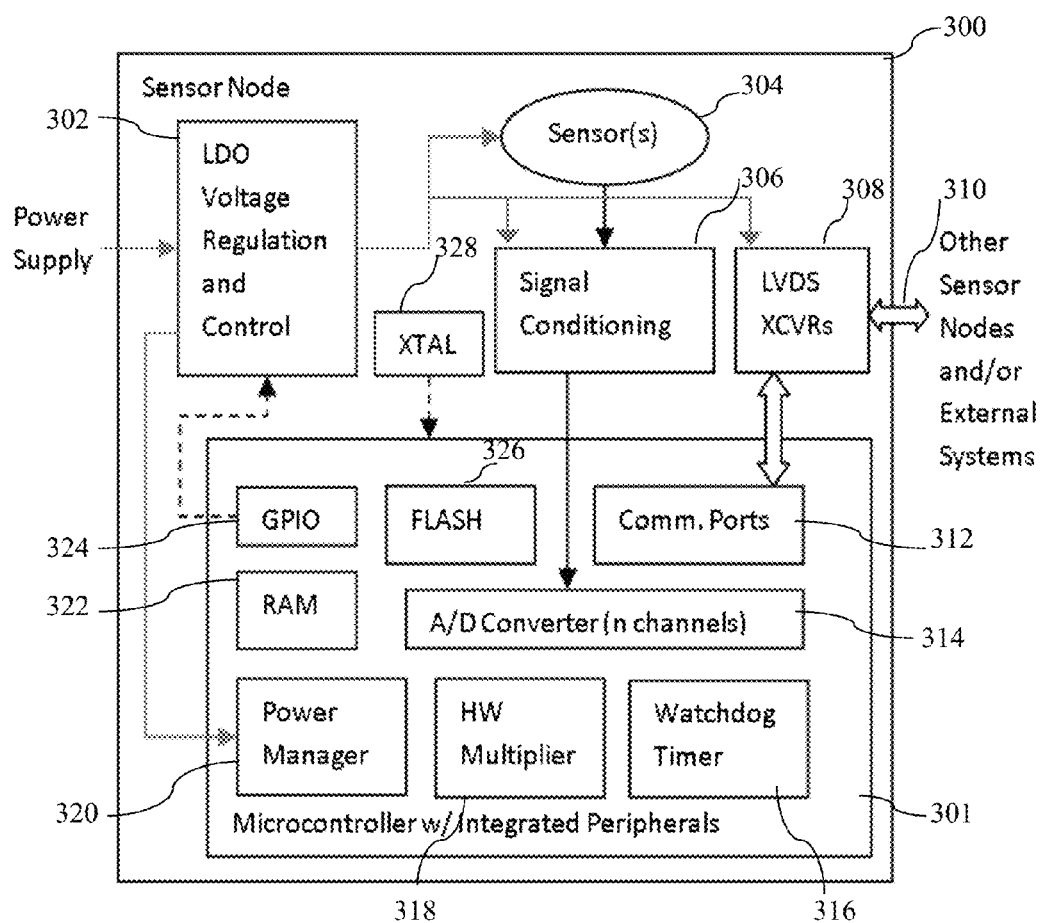
FIG. 3 is a simplified exemplary block diagram of a sensor node, according to some embodiments of the present invention.

FIG. 3 is a simplified exemplary block diagram of a sensor node, according to some embodiments of the present invention. The signal from a sensor 304 is received by a signal conditioning module 306 which provides any gain, offset, and/or analog filtering required prior to digitization by the A/D converter 314. Digitized data are provided to the microcontroller/processor 301. The sensor node 300 is driven by a power supply. A voltage regulator 302 regulates and controls the voltage to the sensor node 300, enabling various components to be deactivated to reduce energy consumption.

Microcontroller/processor 301 includes RAM memory 322 and flash memory 326, which are used to store intermediate data in the sensor node; general purpose I/O (GPIO) 324 and communication ports 312 to communicate data within and outside of the microcontroller/processor 301. A power manager 320 manages power distribution within the microcontroller/processor 301 to further reduce energy consumption. A hardware multiplier 318 provides fast and energy-efficient implementation of the mathematics required by the sensor processing algorithm(s). A watchdog timer 316 automatically resets the microcontroller/processor in case of any faults that cause its program to hang. A transceiver 308 communicates information to/from other sensor nodes or external systems, using LVDS (Low Voltage Differential Signaling) to reduce energy consumption and enhance signal integrity.

In some embodiments, the process/algorithm, running on the sensor nodes (by a respective processor), is generated automatically from a specification of collective behavior, such as from geometry and information flow. One way of accomplishing this is to associate each collective operation with a distributed implementation process/algorithm, and to associate each method for composing collective operations with an equivalent method for composing distributed implementations. For example, this approach may be embodied by specifying collective operations (such as integration over a surface region of sensors, or flow of information along a shortest path between two regions) in the Proto™ programming language. A program thus specified is a functional composition of mathematical operations on fields over geometric manifolds, such as the surface of a person's body. Established transformation methods embodied in the "MIT Proto™" compiler and virtual machine are then capable of transforming any Proto™ language program into a distributed algorithm that approximates the collective specification, such as would be suitable for execution on a collection of networked sensor nodes as described above.

Figure 4:
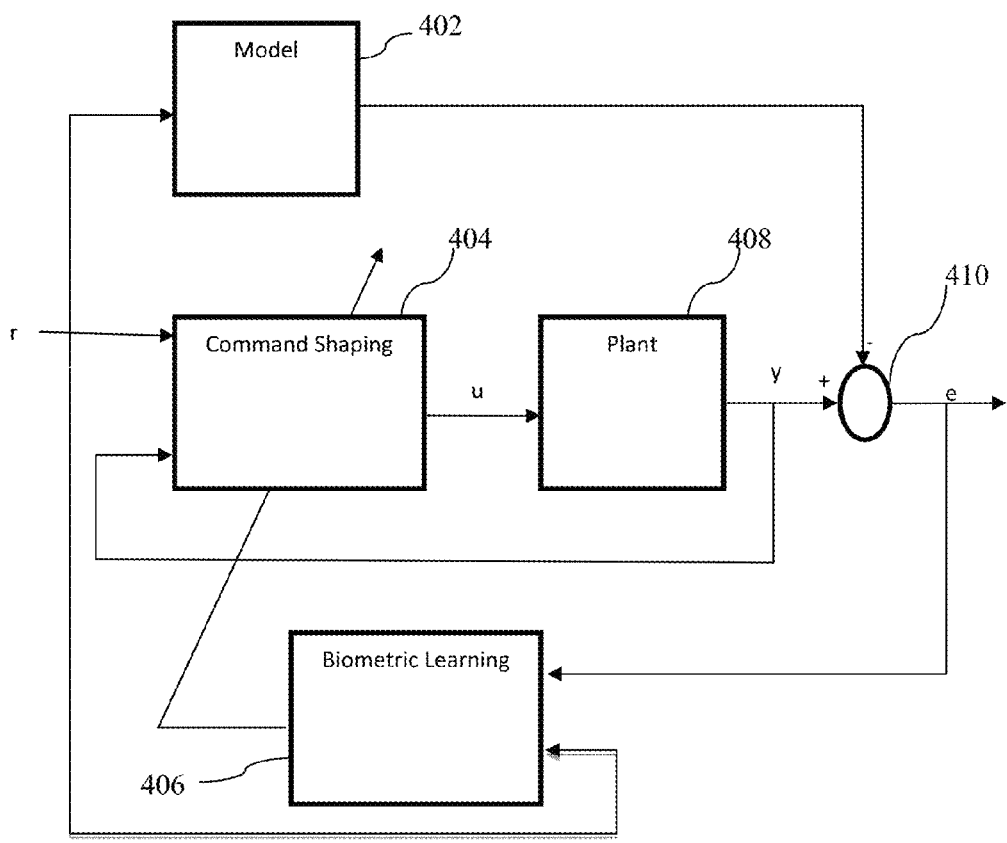
FIG. 4 shows a simplified exemplary block diagram for signal processing and actuator control, according to some embodiments of the present invention.

FIG. 4 shows a simplified exemplary block diagram for signal processing and actuator control, according to some embodiments of the present invention. The plant 408 represents the actual physical system that one desires to affect. This may represent a localized area (e.g. ankle), a collection of areas (e.g. full leg) or the entire body. In typical embodiments, the plant includes the actuation mechanisms and the suite of sensors in the associated body suit. In some embodiments, three processing paths shown in the figure accept reference information r that defines what actions are being commanded. This command may be derived from the sensors through a process that estimates what movement or action is being performed by the person.

For the physical path that includes the real plant 408, a command shaping module 404 properly synchronizes the actuators to achieve the desired result, such as providing an effort assist while running or lifting, and issues commands u to the actuators in the plant 408. A model 402 that represents the total desired system characteristics provides a reference against which to compare (410) the actual system (404 and 408 combined). The differences in comparison 410 between actual and desired responses are used in a biometric learning process 406 that tunes the command shaping to better achieve the desired behavior. This biometric learning provides an extensive ability to tune the system performance to each individual and their current condition. For example, it can adapt the timing and distribution of actuator force assists to compensate for changes in gait that may occur over time.

For example, in some embodiments, hip, knee and ankle actuation may be utilized to provide a mobility assist for a running action. As the person becomes more fatigued over time, his/her pace may slow, form may shift and compliance during the impact portion of the gate may increase. Through the many detailed sensors (e.g. muscle activation manifold) and aggregate state estimates (e.g. fatigue level), the system is capable of identifying these changes and modifying the timing and force levels of the actuators to improve form and increase assist level, increase ankle stiffness during impact to reduce injury risk and assign an estimated fatigue level for the person. Using the distributed sensing and actuation, the system modifies the model of the person to reflect the person's current kinematic form. Furthermore, these metrics can adapt the nominal model to have, for example, a 0.6 second gate time instead of 0.5 seconds. This way, the open loop distributed command shaping applies an appropriate assist based upon the person's current detailed and aggregate state measurements.

In some embodiment, the invention uses (e.g., multivariable) adaptive processing to tune the shape and distribution to command a system of actuators and sensors. Several known techniques may be used for adaptive control. For example a Linear Quadratic Gaussian (LQG) controller is an observer-based control of simple multivariable models that uses distributed actuation and sensing to perform a task; a Least Mean Square (LMS) adaptation technique may tune model parameters and perform system identification; an LMS Filtered-X technique may be used to control complex dynamics with respect to a reference command ("X" notation); and beam-forming techniques may be used to group sets of actuators and sensors to practical basic functions (e.g. "walking configuration").

In some embodiment, the system/garment of the present invention is adaptive in both its control of external devices and its ability to measure high-dimensional goal manifolds. This adaptive system is robust to the shifting and imprecision of sensors on the skin/garment. The adaptive system also accommodates variations in a single user/wearer's performance. The human body has variable range of motion, muscle strength and responsiveness, so the degrees of freedom being measured by the suit while performing a goal changes via the time of day, the temperature, and the health of the subject along with other events. This high dimensional dynamic data piece is referred to as the goal manifold. The calibration data taken after the subject initializes the system provides a baseline for the model to use, however, the model may be updated throughout the subject's usage of the system.

The original goal manifold for walking, for instance, is a starting point. The difference between this manifold and the measured manifold is utilized to update the stored model with more recent information to correspond with the reality. In adapting to the garment's positioning over the epidural manifold, the feature vectors is updated to correspond with the sensor streams that contain the highest signal to noise ratio in identifying the current goal manifold. The adaptive control for external devices allows for the system to respond to feedback given by the suit itself or other data streams coming from the external devices. If adequate information is available, that feedback is used to optimize the performance of the external device to maximize its value to the subject.

This system of distributed sensors and sensor nodes is adaptable to hardware and communication faults, that is, in most cases, loss of a node or communication link between nodes is effectively a coarsening of the geometric approximation. Periodic updates maintaining the connection between each node and its neighbors suffice to discover these types of faults. Following discovery of a fault, the surviving devices reapportion the surface that each represents. Certain faults may cause larger-scale disruption, e.g., the loss of a node in the hip area that was serving as a relay for information from the knee to reach the shoulders. In this case, an implementation of that distributed geometric algorithms that uses self-stabilizing geometric algorithms based on constant rate factor (CRF), such as CRF-Gradient, ensures that if any valid geometric construct exists following the fault (e.g., any path from knees to shoulders), it is rapidly identified and used.

In a spatial computing approach, sensors (and their data) are considered to be acting as part of the same unit whenever they are close to one another (a parameter that can be set at the system level depending on the application) and are moving together, for example, their most recent motions were within a certain speed, distance and/or degrees direction. For instance, a muscle movement can be detected by multiple sensors, and each sensor can detect multiple muscle movements, so a good place to start is aggregating detections information from the sensors into the processors. That is, each sensor node may run a computation for each muscle movement (for example, circumferential changes in muscle) it detects, and computations share information with neighboring computations only if they are about the same muscle movement.

This can be determined for each neighbor of a sensor by comparing the relative position of the local detection with the sum of the neighbor's current value for its detection and the neighbor's relative position. Each muscle movement can be estimated geometrically by tracking what sensors are entering and exiting its detection region.

To cluster muscle movements into units, for each muscle movement, a region of every point within a certain distance is selected. This ensures that if two muscle movements are within a certain distance of one another (and therefore close enough to be in the same unit), there is at least one point where their regions overlap. These regions can be constructed by measuring the distance to the muscle movement and testing whether the distance is less than the certain distance, producing an indicator field. A function mapping is performed for each point in space to a Boolean, true for points in the region and false for points not in the region. For those sensors that cannot detect the muscle movement directly, distance can be estimated by applying the triangle inequality, for example, the minimum over all neighbors of the sum of a neighbor's current value for the estimate and the range to the neighbor.

Sensors that know the current movement (e.g., speed and bearing) estimates for a muscle movement can supply them to others in the region by taking the gradient of the distance estimates. This produces a vector field indicating which direction the estimates should flow from the source. Given recent speed and bearing estimates, points where two regions intersect can be compared to determine whether the two muscle movements are part of the same unit.

Finally, the number of muscle movements in a unit and its aggregate velocity can be computed with surface integrals over the union of regions for nodes in the same unit. Accordingly, how a distributed algorithm might be formulated in terms of geometric computations is demonstrated. More sophisticated applications, for example, incorporating reliability estimates from sensors or accounting for erratic or large movements in the unit definition, can be implemented with more sophisticated geometric computations.

Figure 5:
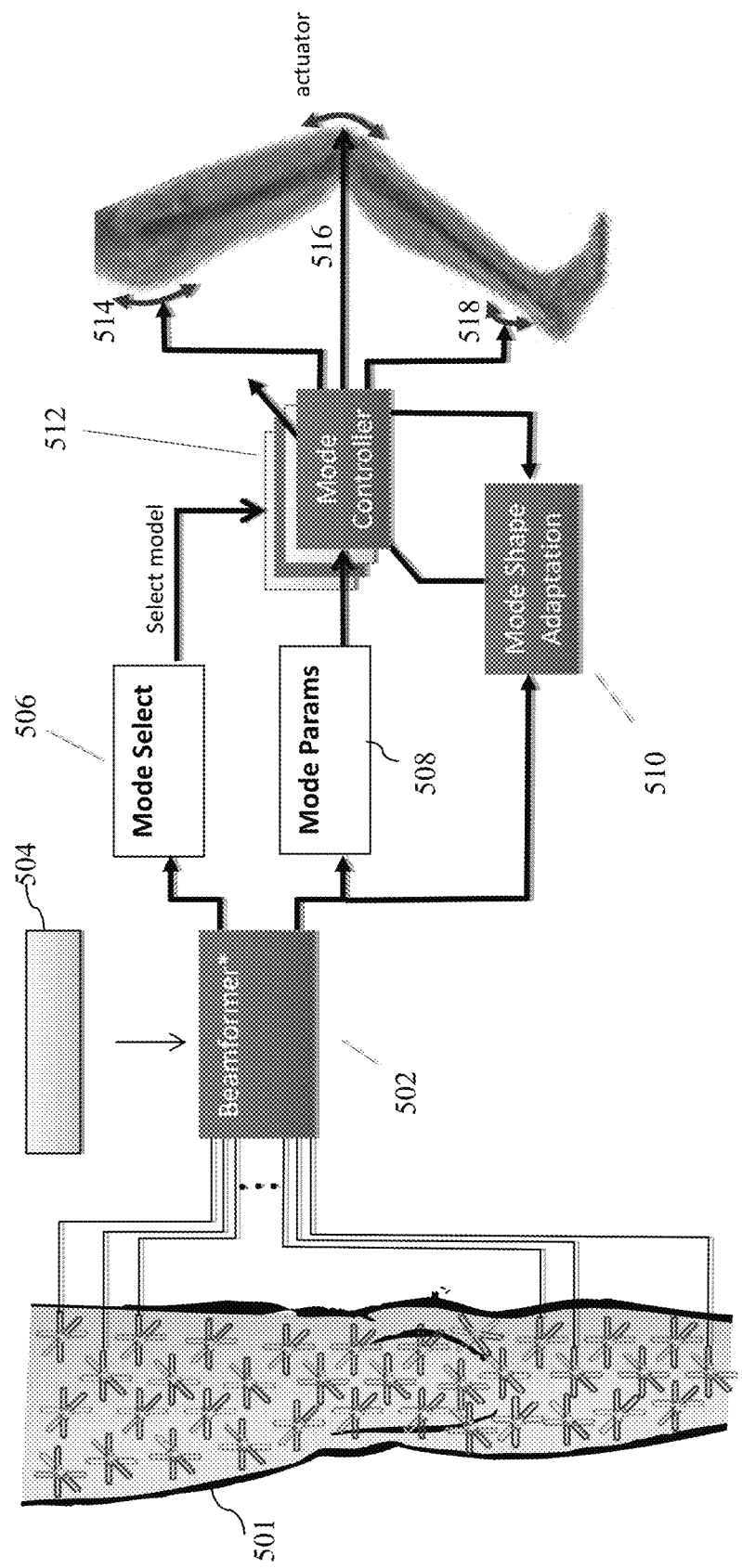
FIG. 5 shows a simplified exemplary block diagram for a control function, according to some embodiments of the present invention.

FIG. 5 shows a simplified exemplary block diagram for a control function, according to some embodiments of the present invention. A garment 501 with distributed sensors and processors provides localized information about a portion of the body. This information is processed by a beamformer 502 that serves several functions. For instance, the beamformer 502 provides a scoring mechanism against basis functions 504 that are characteristic to the different capabilities of the garment or a larger set of garments. These basis functions may include processed metrics, such as, cycle time and higher frequency muscle motion (e.g. impact vibrations) to produce key features that are used in a weighted multiple evidence comparison scheme, such as, the Dempster-Shafer method.

In some embodiments, features may also be a manifold comparison using an inner product of measured distribution versus candidate manifold shapes. For example, a heavy lifting motion will have certain muscles all activated in phase, a high level of detected effort, and slow movement time. A simple standing action would have a lower level of effort and a running action would have different phasing of the muscles and a different motion speed. In a Dempster-Shafer process, each candidate action would have a statistical likelihood of a feature value being associated with the action. Continuing with the heavy lift example, consider the three candidate features of high muscle activation, phase (synchronization) of muscle activation and action speed. From a probability perspective, a weighted statistical algorithm could assign a weighted probability of 1 for a slow action speed for heavy lift and standing actions but only a 0.1 for a running action. Table 1 shows an example of how such features could be used to score measured information against candidate actions for this simple example. The result then scores a heavy lift as the most probable action being performed. Additional features would improve discrimination among the actions.

TABLE 1

| Example Measured Feature | | Example Basis Function Score | | |
| --- | --- | --- | --- | --- |
| Description | Value | Heavy Lift | Standing | Running |
| Muscle activation intensity | High | 1 | .3 | 1 |
| Activation phase | In-phase | 1 | 1 | 0.3 |
| Action Speed | slow | 1 | 0.9 | 0.1 |
| Simple Total | | 3 | 2.2 | 1.4 |

This enables the larger control system to select a particular mode 506 (e.g. running) and parameters 508 associated with that mode (e.g. gait). The beamformer 502 also provides information for mode shape adaptation 510, or tuning. The mode selector 506 chooses which dynamic mode controller 512 to employ to optimize the estimated action. This controller issues distributed actuation commands to notional actuation mechanisms 514, 516 and 518.

Figure 6:
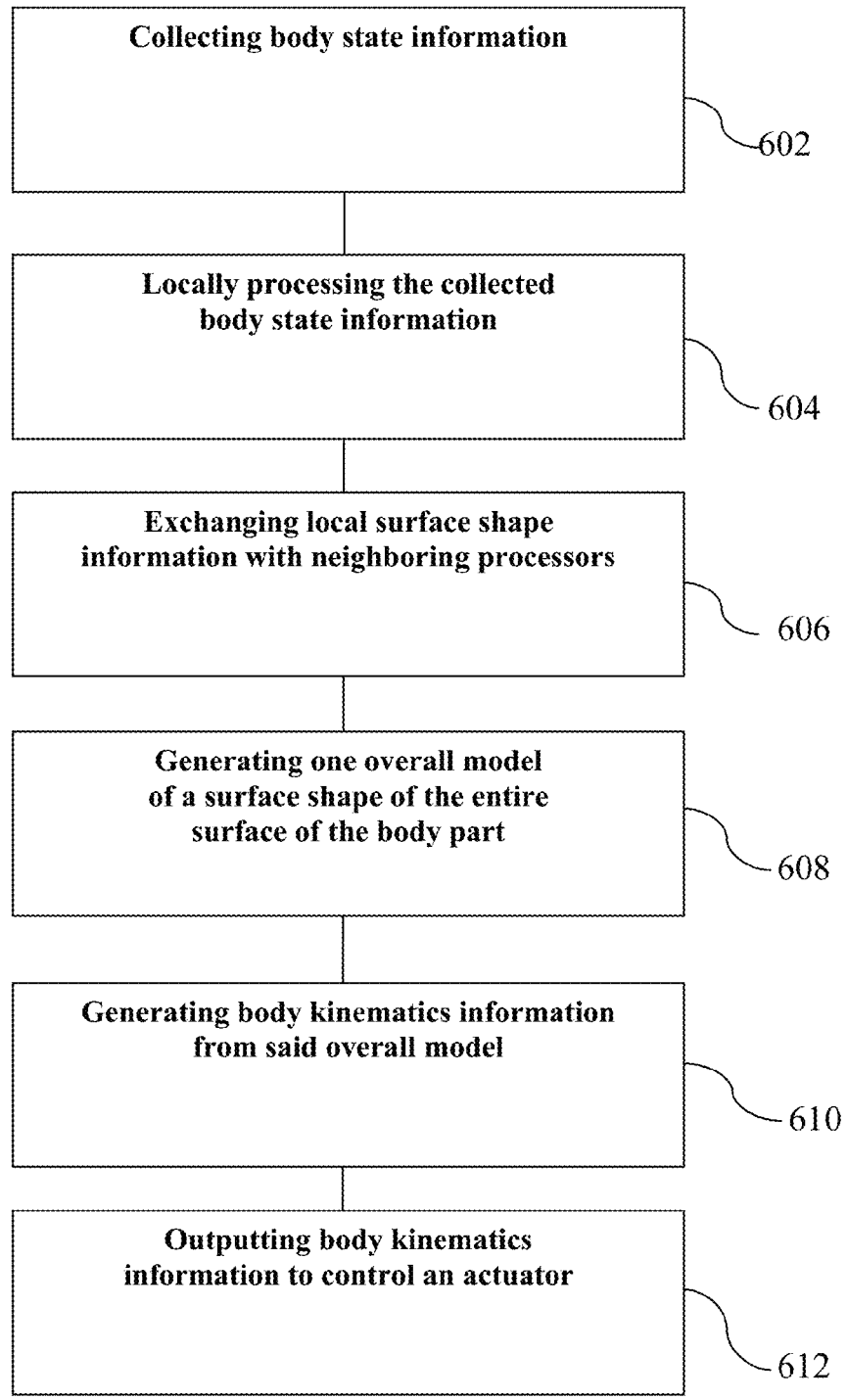
FIG. 6 depicts a simplified process flow for detecting body kinematics, according to some embodiments of the present invention.

FIG. 6 depicts a simplified process flow for detecting body kinematics, according to some embodiments of the present invention. As shown in block 602, body state information is collected from a plurality of local surface areas of a body part that is covered by the garment. The information is collected from a plurality of sensors that are distributed throughout the garment covering the body part. The body state information may include parameters and features of interest, for example, skin surface temperature, electrical nerve impulses, and whether a person has been at rest or is warmed up. The body state information can be processed over time to estimate more complex bio-state information such as fatigue and injury. The collected body state information of local surface areas are then processed locally and in real time (by a plurality of processors distributed throughout the garment) to determine a local surface shape of the surface of a portion of the body part covered by respective local surface areas, in block 604. This local surface shape information represents a model for each local area of the body part that is covered by one or more sensors and a corresponding distributed processors. The determination of this local surface shape information may be based on geometric computation or spatial computing approach, as described above.

In block 606, local surface shape information is exchanged with neighboring processors. In some embodiments, all of a large portion of the distributed processors have the local surface shape information for all or most of the sensors. In block 608, a single overall model of a surface shape of the entire surface of the body part that is covered by the garment is generated from the distributed local surface shape information. In some embodiments, any one of the distributed processors is capable of generating this single overall model based on the localized body state information that it receives from the other distributed processors. The generation of this single overall model may also be based on geometric computation or spatial computing approach, as described above.

Optionally, in block 610, the overall model is used to generate body kinematics information. However, the overall model information may be used in other applications such as generating measures of asymmetry to look for Parkinson's disease and to provide a distributed measurement of the activity in the motor cortex of the brain. In some embodiments, the invention takes (records) snap shots of the overall model at different times and compares the snap shots to determine the overlapped areas and the areas that have changed from one snap shot to the next snap shots. Based on the comparison results, the invention then generates body kinematics information such as pose, motion and muscle activation, using known image reconstruction techniques. In some embodiments, the overall model includes information about rate of change of the surface shape over time, and the invention generates body kinematics information using the rate of change of the surface shape information included in the model. Other known techniques may be used to generate the body kinematics information from the overall model.

The generation of the body kinematics information may be performed within the garment by any one or the distributed processor (since every processor has all the information it needs); in a central processor within the garment; or by one or more devices external to the garment. In some embodiments, each of the distributed processors is configured to perform adaptive processing and change the degrees of freedom being measured by the plurality of sensors, according to the time of day, the temperature, and the health of the subject wearing the garment.

Optionally, in block 612, the body kinematics information is outputted, for example, to a controller, to control an actuator. In some embodiments, at least one of the distributed processors is configured to adaptively control said actuator and respond to feedback provided by the plurality of sensors, sensor nodes and/or data streams coming from external devices.

The following describes an exemplary detail technique for estimating pose from strain data. First, locations for sensors on a nominal body model are presumed for a specific joint. This way, the three dimensional locations of sensors on body define an N×3 matrix P. Strain sensors provide an estimate of distance between presumed sensor locations on a nominal body mapping X, which is an N×N sparse matrix of estimated distances. Sensors provide a measurement of that matrix, that is, Z, an N×N sparse matrix of measured differences.

From these presumed prior locations and measured distances, error corrections are computed as:

$$d = Z - x$$

The model then converts the corrections to produce an N×N×3 perturbation tensor S. This tensor S is then applied along presumed arcs to create perturbations back to the position matrix P, which is updated to correct for the measured errors. This process is iterated until the solution becomes stable. In some embodiments, this process is executed only around joints, with the complete body pose being then derived through application to a standard body model of joints and bones. In some embodiments, the process may be applied to entire limbs or body regions as a means of detecting fracture or other damage to the body.

As body pose evolves over time, lines of change and movement are examined and compared against a body model to ascertain sensor placement with respect to specific body structures. In this way the position matrix P can be updated.

It will be recognized by those skilled in the art that various modifications may be made to the illustrated and other embodiments of the invention described above, without departing from the broad inventive scope thereof. It will be understood therefore that the invention is not limited to the particular embodiments or arrangements disclosed, but is rather intended to cover any changes, adaptations or modifications which are within the scope and spirit of the invention as defined by the appended claims.

What is claimed is:

1. A body garment for detecting body kinematics comprising:
   a plurality of sensors distributed throughout the garment, each sensor being configured to sense body state information from a local surface area of a body part covered by the garment; and
   a plurality of sensor nodes in proximity to the plurality of sensors respectively, each sensor node including a processor and configured to receive sensing body state information from at least one of the plurality of sensors;
   wherein each processor is configured to receive body state information locally from one or more sensors in proximity to said each processor; to utilize the information to determine a local surface shape of the surface of a portion of the body part covered by said one or more sensors; and to exchange local surface shape information with neighboring sensor nodes, and
   wherein at least one processor of at least one sensor node utilizes the local surface shape information received from the sensor nodes to generate one overall model of a surface shape of the entire surface of the body part covered by the garment.

2. The body garment of claim 1, wherein said at least one processor of at least one sensor node is further configured to generate body kinematics information from said overall model.

3. The body garment of claim 2, wherein at least one of the plurality of the processors is further configured to output said body kinematics information to control an actuator.

4. The body garment of claim 3, wherein said at least one of the plurality of the processors is further configured to adaptively control said actuator and respond to feedback provided by the plurality of sensors, sensor nodes or data streams coming from external devices.

5. The body garment of claim 2, wherein said at least one processor is configured to generate body kinematics information by taking snap shots of overall model at different times and compare the snap shots.

6. The body garment of claim 2, wherein said overall model includes a rate of change of the surface shape over time, and wherein said at least one processor is configured to generate body kinematics information using said rate of change of the surface shape.

7. The body garment of claim 2, wherein said body kinematics information include one or more of body pose, gait, and muscle activation of the subject wearing the garment.

8. The body garment of claim 2, wherein at least one of the plurality of the processors includes an interface for driving one or more of an actuator for mechanical assisting for walking, running or integration of a prosthetic limb, a haptic feedback device for delivering injury warnings, a biomechanical system for analyzing metabolic activity or athletic load endured by a subject wearing the garment, and a health monitoring system.

9. The body garment of claim 1, wherein said body state information include one or more of skin surface temperature, electrical nerve impulses, and whether a person has been at rest or is warmed up.

10. The body garment of claim 1, wherein the body garment comprises of a plurality of different portions, each portion configured to be coupled to and decoupled from the other portions.

11. The body garment of claim 1, wherein a first subset of the plurality of sensor nodes located on critical regions of the body part is configured to operate faster and denser than a second subset of the plurality of the sensor nodes located on stable regions of the body part.

12. The body garment of claim 1, wherein the plurality of sensors are configured in a plurality of manifolds, each manifold of group of sensors including a set of similar and related sensors in close proximity of each other that respond in an ordered distribution, wherein the body garment is capable of losing some fraction of sensors or displacement of some of the sensors on the garment and still generate said body state information.

13. The body garment of claim 1, wherein each processor is configured to perform adaptive processing to tune the local surface shape to exchange the tuned local surface shape information with neighboring sensor nodes to commend a plurality of actuators.

14. The body garment of claim 1, wherein each processor is configured to change degrees of freedom being measured by the garment according to the time of day, the temperature, and the health of the subject wearing the garment.

15. The body garment of claim 1, wherein said each processor is further configured to determine the local surface shape of the surface of a portion of the body part covered by said one or more sensors using geometric processing.

16. A method for detecting body kinematics comprising:
collecting body state information from a plurality of local surface areas of a body part covered by a garment, from a plurality of sensors distributed throughout the garment covering the body part;
locally and in real time processing the collected body state information of local surface areas to determine a local surface shape of the surface of a portion of the body part covered by respective local surface areas, by a respective one of a plurality of distributed processors;
exchanging local surface shape information with neighboring processors; and
generating one overall model of a surface shape of the entire surface of the body part covered by the garment from the distributed local surface shape information.

17. The method of claim 16, further comprising generating body kinematics information from said overall model.

18. The method of claim 17, further comprising receiving feedback from the plurality of distributed processors or from external devices; and using said feedback and said body kinematics information to adaptively control an actuator.

19. The method of claim 16, wherein said overall model includes a rate of change of the surface shape over time, and further comprising generating body kinematics information using said rate of change of the surface shape.

20. The method of claim 16, further comprising changing degrees of freedom being measured by the plurality of processors according to the time of day, the temperature, and the health of the subject wearing the garment.

* * * * *